United States Patent [19]

Scholes et al.

[11] 4,262,124

[45] Apr. 14, 1981

[54] BICYCLIC LACTAMS AND PROCESS FOR THEIR PREPARATION

[75] Inventors: Gary Scholes; Frank Baardman, both of Amsterdam, Netherlands

[73] Assignee: Shell Oil Company, Houston, Tex.

[21] Appl. No.: 147,419

[22] Filed: May 6, 1980

Related U.S. Application Data

[63] Continuation-in-part of Ser. No. 117,698, Feb. 1, 1980, abandoned.

[30] Foreign Application Priority Data

Feb. 23, 1979 [GB] United Kingdom ................. 6412/79

[51] Int. Cl.³ ............................................. C07D 295/10
[52] U.S. Cl. ........................................ 546/183; 71/95
[58] Field of Search ........................................... 546/183

[56] References Cited

U.S. PATENT DOCUMENTS 4,047,930  9/1977  Kerr ........................................ 71/95

FOREIGN PATENT DOCUMENTS 46-14731  4/1971  Japan ..................................... 546/183

OTHER PUBLICATIONS

Chemical Abstracts, Eighth Collective Index, (Amino-Benzimidazolid), 1967–1971, p. 3132S (1972).
Chemical Abstracts, Ninth Collective Index, (Amet-Benzenamine,phenoxy), 1972–1976, p. 2468CS (1979).
Julia et al., Chemical Abstracts, vol. 62, cols. 5299–5300 (1965).
Julia et al., Chemical Abstracts, vol. 66, abst. 85867y (1967).
Chemical Abstracts, vol. 75, abst. 36972f (1971).
Chemical Abstracts, vol. 78, abst. 111524d (1973).

*Primary Examiner*—John D. Randolph

[57] ABSTRACT

A process for preparing the cis-racemate of 3-azabicyclo-(3.1.0)hexane-2-carboxylic acid, and certain novel intermediates involved therein.

5 Claims, No Drawings

BICYCLIC LACTAMS AND PROCESS FOR THEIR PREPARATION

This application is a continuation-in-part of application Ser. No. 117,698 filed on Feb. 1, 1980, abandoned.

BACKGROUND OF THE INVENTION 3-azabicyclo(3.1.0)hexane-2-carboxylic acid, also known as methanoproline, and certain of its esters, are known to inhibit (suppress) pollen formation in cereal grains: U.S. Pat. No. 4,047,930 (the acid being designated therein as 2-carboxy-3,4-methanopyrrolidine). Methanoproline exists in the forms of two geometric (i.e., cis and trans) isomers. Each of these isomeric forms exists in the forms of optical isomers. The racemic mixtures of both of the geometric isomeric forms inhibit pollen formation in cereal grains. However, it has been found that with respect to some cereal grains the cis racemate is more active for that purpose than the trans racemate. Accordingly, it is desirable that there be available a method for preparing the cis racemate of methanoproline.

DESCRIPTION OF THE INVENTION

It has now been found that the cis-racemate of 3-azabicyclo(3.1.0)hexane-2-carboxylic acid can be prepared as follows:

(1) 3-hydroxyimino(3.1.0)hexane (Corey, et al., Journal of the American Chemical Society, vol. 84, pp. 1782–7 (1963)) is treated with thionyl chloride, to effect a Beckman rearrangement.

(2) The resulting bicyclic lactam, 3-azabicyclo(4.1.0-)heptane-4-one (I), is treated with benzoyl chloride in the presence of a hydrogen chloride acceptor.

(3) The resulting 3-benzoyl-3-azabicyclo(4.1.0)heptan-4-one (II) is halogenated.

(4) The resulting 5-halo-3-benzoyl-3-azabicyclo(4.1.0)heptan-4-one (III) is treated with an acid.

(5) The resulting 5-halo-3-azabicyclo(4.1.0)heptan-4-one (IV) is treated with alcoholic alkali metal to give the racemic mixture of the cis isomeric form of 3-azabicyclo(3.1.0)hexane-2-carboxylic acid.

In terms of structural formulae of the intermediates involved, the reactions are:

(1) 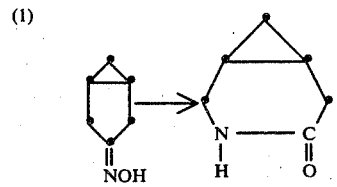

(2) 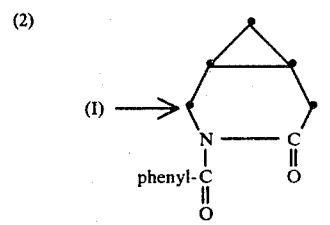

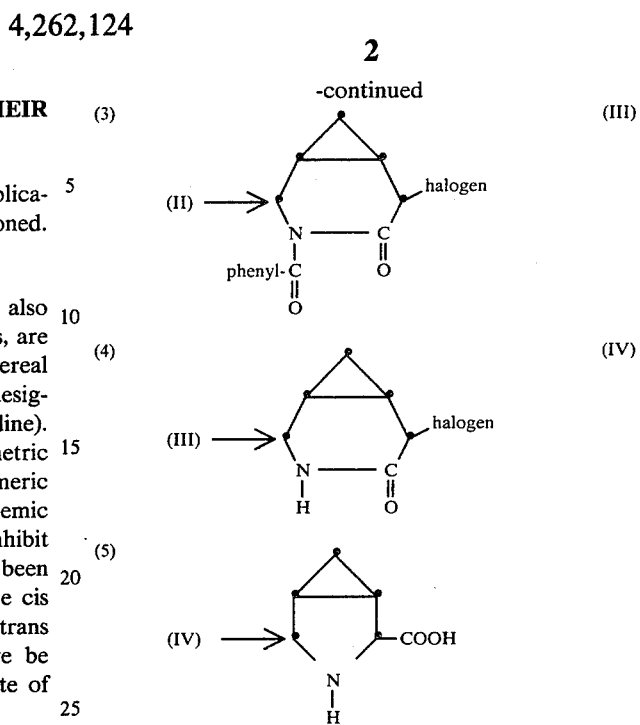

In the halogen-substituted compounds, as in 3-azabicyclo-(3.1.0)hexane-2-carboxylic acid, the compounds exhibit both optical and geometric isomerism. Geometric isomerism with respect to the halogen atom or carboxyl moiety is of cis/trans nature, with respect to the configuration of the halogen atom or carboxyl moiety and the three-membered bridging moiety. For each such geometric isomer, a pair of optical isomers exists, due to the asymmetry of the carbon atom to which the halogen atom or carboxy moiety is bonded, resulting in the cis- and trans-racemic mixtures.

To simplify this disclosure, avoiding unnecessary repetition, the cis-racemates will hereinafter be designated as simply the appropriate cis compounds.

In the halogen-substituted intermediate, the halogen is middle halogen—i.e., chlorine or bromine, chlorine being preferred.

The intermediate compounds are novel and are claimed herein.

Conversion of the 3-hydroxyimino(3.1.0)hexane to 3-azabicyclo-(4.1.0)heptan-4-one is conducted as for a conventional Beckmann rearrangement, and is illustrated in a particular instance in part (a) of Example 1, hereinafter.

Halogenation of 3-azabicyclo(4.1.0)heptan-4-one can be accomplished by conventional techniques, using any conventional halogenating agent. Suitable chlorinating agents include sulphuryl chloride, phosphorus pentachloride, N-chlorosuccinimide, alkali metal hypochlorites, and molecular chlorine. Preference is given to the use of sulphuryl chloride or phosphorus pentachloride as chlorinating agent. Suitable brominating agents include sulphuryl bromide, phosphorus tribromide, bromine, N-bromo-succinimide, and alkali metal hypobromites. Preference is given to the use of sulphuryl bromide.

The halogenation can be carried out conveniently at temperatures up to 150° C. For chlorination, temperatures between 50° and 80° C. are preferred. Higher temperatures are normally required to introduce a bromine atom at the 5-position in the bicyclic lactam.

The presence of the benzoyl moiety in the starting bicyclic lactam leads to the result that the 5-monohalo compounds are selectively obtained in high yield.

The halogenation is preferably carried out in the presence of an inert solvent. Suitable solvents include alkanes, cycloalkanes, and halogenated alkanes and alkenes, for example, hexane, heptane, cyclopentane, cyclohexane, methylene dichloride, chloroform, carbon tetrachloride, dichloroethane, trichloroethylene and perchloroethylene. Also mixtures of solvents, e.g., a mixture of carbon tetrachloride and cyclohexane, can be used.

The halogenating agent can be applied in a stoichiometric amount with respect to the lactam. Good results are normally obtained using a slight excess of halogenating agent, e.g., 5–20% mole, per mole of compound to be halogenated.

The 5-monohalo compound can be isolated from the reaction mixture by any conventional technique, e.g., by removal of the solvent or solvent mixture followed by one or more wash treatments and final drying. It is also possible and sometimes advantageous to use the crude product obtained in the halogenation step in situ without purification.

The replacement of the benzoyl moiety by a hydrogen atom can be carried out conveniently by treating the 5-monohalo compound either after isolation or as such in the crude reaction product with a strong acid. Suitable acids include mineral acids such as sulphuric acid and hydrochloric acid, and strong organic acids such as trifluoroacetic acid. Good results have been obtained using concentrated sulphuric acid. Usually the reaction will be carried out at ambient or somewhat elevated temperatures, e.g., temperatures up to 100° C.

The 5-halo-3-azabicyclo(4.1.0)heptan-4-one product can be obtained by using conventional working-up techniques such as neutralizing the reaction mixture followed by extraction with a suitable solvent. Evaporation of the solvent will then give the product, which may be further purified, e.g., by recrystallization techniques if necessary.

The 5-halo-3-azabicyclo(4.1.0)heptan-4-one can be converted to 3-azabicyclo(3.1.0)hexane-2-carboxylic acid by treating it with an alkali metal in the presence of an alcohol and acidifying the resulting mixture. The manner in which this conversion, and the desired product is isolated, are illustrated in part (d) of Example 1.

Preparation of the cis racemate of methanoproline by practice of the invention in a particular instance is described in Example 1. In each instance, the identity of the product involved was confirmed by appropriate chemical and spectral analyses.

EXAMPLE 1

(a) Preparation of
3-benzoyl-3-azabicyclo(4.1.0)heptan-4-one (II)

To an ice-cold solution of 6.5 g of 3-hydroxyimino(3.1.0)hexane in 40 ml of dry ether was added a solution of 13 ml of thionyl chloride in 40 ml of dry ether over a period of 30 minutes while stirring. A white solid separated which gradually turned brown. The stirring was continued at room temperature for 5 hours. After evaporation of the solvent and excess thionyl chloride under reduced pressure, ice was added to the residue. The aqueous solution formed was made alkaline by the addition of a dilute NaOH solution and then extracted with methylene dichloride. The extract was dried over anhydrous magnesium sulfate and then boiled with Norit to remove most of the brown discoloration. Evaporation of the solvent then left 3-azabicyclo(4.1.0)heptan-4-one (I), as a light brown residue which solidified on standing.

To the product were added 6.3 g of benzoyl chloride and 5.4 g of dimethylaniline, and the mixture was stirred at 70° C. for three hours. The mixture then was allowed to cool, and poured onto an ice/dilute hydrochloric acid mixture and extracted with methylene dichloride. The collected organic layers were dried over anhydrous magnesium sulfate. The solvent was evaporated and last traces of excess benzoyl chloride were removed by pumping with a vacuum pump to give (II).

(b) Preparation of
5-chloro-3-benzoyl-3-azabicyclo(4.1.0)heptan-3-one (III)

A mixture of 5 g of II and 3.5 g of sulphuryl chloride in a mixture of 1 ml of carbon tetrachloride and 3 ml of cyclohexane as solvent was heated under reflux for two hours. After removal of the solvent mixture by evaporation, 10 ml of absolute ethanol was added and removed by evaporation one hour later to obtain a dry product (III) which was not purified further.

(c) Preparation of
5-chloro-3-azabicyclo(4.1.0)heptan-4-one (IV)

5 g of III, obtained in experiment (b), was added to 10 ml of 96% sulphuric acid and stirred for three hours at 80° C. After cooling, the reaction mixture was neutralized with ammonium hydroxide and extracted with methylene chloride. After evaporation of the solvent the residue was purified by passing over a column of neutral alumina and eluting with diethylether to give IV, as a yellow solid. Recrystallization from diethyl ether/pentane gave IV, as pale yellow crystals. It was characterized as the trans isomer on the basis of spectral analysis.

(d) Preparation of 2-carboxy-3-azabicyclo(3.1.0)hexane 0.9 g of IV prepared in experiment (c) was refluxed for 16 hours in t-butanol containing 0.5 g potassium. The reaction mixture was allowed to cool, the solvent was evaporated under reduced pressure and the residue was poured into 20 ml of water. Dilute (4 N) hydrochloric acid was added until the solution was acidic and then extracted thrice with methylene chloride. The water layer was then passed over a column filled with Dowex 50W-X8 ion-exchange resin. Eluting the resin with ammonium hydroxide then gave the cis isomer of 3-azabicyclo(3.1.0)hexane-2-carboxylic acid.

I claim:

1. 3-benzoyl-3-azabicyclo(4.1.0)heptan-4-one.
2. 5-halo-3-benzoyl-3-azabicyclo(4.1.0)heptan-4-one wherein "halo" is chlorine or bromine.
3. A compound of claim 2 wherein "halo" is chlorine.
4. 5-halo-3-azabicyclo(4.1.0)heptan-4-one wherein "halo" is chlorine or bromine.
5. A compound of claim 4 wherein "halo" is chlorine.

* * * * *